United States Patent
Blythe et al.

(10) Patent No.: US 7,265,370 B2
(45) Date of Patent: Sep. 4, 2007

(54) SENSING LIGHT

(75) Inventors: Michael M. Blythe, Albany, OR (US);
Wyatt A. Huddleston, Allen, TX (US);
Gregory W. Blythe, Philomath, OR (US); Jeffrey L. Thielman, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 98 days.

(21) Appl. No.: 11/116,805

(22) Filed: Apr. 28, 2005

(65) Prior Publication Data

US 2006/0243928 A1 Nov. 2, 2006

(51) Int. Cl.
*G06K 5/00* (2006.01)
*G03B 21/10* (2006.01)

(52) U.S. Cl. ............... 250/566; 250/221; 250/224; 250/226; 345/156; 353/74

(58) Field of Classification Search ............... 250/566, 250/221, 224, 226; 356/391, 402, 71; 345/175, 345/156; 353/74
See application file for complete search history.

(56) References Cited

U.S. PATENT DOCUMENTS

| | | | | |
|---|---|---|---|---|
| 3,253,365 A * | 5/1966 | Calderon | ............ | 446/259 |
| 4,098,940 A | 7/1978 | Groh et al. | | |
| 4,381,892 A | 5/1983 | Someya | | |
| 4,792,667 A | 12/1988 | Chen | | |
| 5,072,128 A | 12/1991 | Hayano et al. | | |
| 5,243,405 A | 9/1993 | Tichenor et al. | | |
| 5,444,263 A | 8/1995 | Mastnak | | |
| 5,455,906 A * | 10/1995 | Usuda | ............ | 345/536 |
| 5,659,163 A | 8/1997 | Lagan et al. | | |
| 5,659,378 A | 8/1997 | Gessel | | |
| 5,831,601 A * | 11/1998 | Vogeley et al. | ............ | 345/175 |
| 5,874,742 A | 2/1999 | Romano | | |
| 5,892,239 A * | 4/1999 | Nagase | ............ | 250/556 |
| 5,898,153 A | 4/1999 | Lagan et al. | | |
| 5,963,280 A | 10/1999 | Okuda et al. | | |
| 5,983,120 A | 11/1999 | Groner et al. | | |
| 6,006,668 A | 12/1999 | Rehmann | | |
| 6,020,944 A | 2/2000 | Hoshi | | |
| 6,104,939 A | 8/2000 | Groner et al. | | |
| 6,301,044 B1 | 10/2001 | Huber et al. | | |
| 6,470,093 B2 | 10/2002 | Liang | | |
| 6,473,165 B1 * | 10/2002 | Coombs et al. | ............ | 356/71 |
| 6,597,454 B1 | 7/2003 | Berg et al. | | |
| 6,606,080 B2 | 8/2003 | Mukao | | |
| 6,656,428 B1 | 12/2003 | Clark et al. | | |
| 6,714,288 B2 * | 3/2004 | Cohen | ............ | 356/71 |
| 6,731,393 B1 | 5/2004 | Currans et al. | | |
| 6,797,366 B2 | 9/2004 | Hanson et al. | | |
| 6,927,844 B2 * | 8/2005 | Higuchi et al. | ............ | 356/71 |

(Continued)

OTHER PUBLICATIONS

A. Hochbaum, Y. Jiang, W. Niu, *Bright Reflective Color Filters Based on Cholesteric Liquid Crystal Polymers*, IDQW'99 (Proceedings of the Sixth International Display Workshops), 379, 1999 (3 pgs.).

(Continued)

*Primary Examiner*—Georgia Epps
*Assistant Examiner*—Christopher M Yealy

(57) ABSTRACT

A method and apparatus senses light reflected off of a surface of an object at angles with respect to incident light.

26 Claims, 4 Drawing Sheets

U.S. PATENT DOCUMENTS

| | | | |
|---|---|---|---|
| 7,103,201 B2* | 9/2006 | Scott et al. | 382/124 |
| 2003/0053013 A1* | 3/2003 | Tanaka | 349/106 |
| 2003/0063772 A1* | 4/2003 | Smith et al. | 382/100 |
| 2004/0051862 A1* | 3/2004 | Alcock et al. | 356/71 |
| 2004/0222366 A1 | 11/2004 | Frick | |
| 2005/0013644 A1 | 1/2005 | Kim | |
| 2005/0024415 A1 | 2/2005 | Claramunt et al. | |
| 2005/0187018 A1* | 8/2005 | Takeda et al. | 463/34 |
| 2005/0245302 A1* | 11/2005 | Bathiche et al. | 463/1 |
| 2006/0109199 A1* | 5/2006 | Yee et al. | 345/1.3 |
| 2006/0203208 A1* | 9/2006 | Thielman et al. | 353/74 |

OTHER PUBLICATIONS

A. Hochbaum, Y. Jiang, *Cholesteric Color Filters—Optical Characteristics, Light Recycling and Brightness Enhancement*, Society of Information Display (SID) Digest, 1063, 1999 (3 pgs.).

Y. Jiang, B. Wilson, A. Hochbaum, J. Carter, *Novel Pigment Approaches in Optically Variable Security Inks Including Polarizing Cholesteric Liquid Crystal (CLC) Polymers*, Optical Security and Counterfeit Deterrence Techniques IV, SPIE 4677, 2002 (8 pgs.).

Chelix Tech Corp., *Pigment Technology*, www.chelix.com/products, 2002-2003 (I pg.).

Chelix Tech Corp., *Optical Components*, www.chelix.com/products, 2002-2003 (2 pgs.).

Chelix Tech Corp., *How Pigment Technology Works*, www.chelix.com/products, 2002-2003 (2 pgs.).

Chelix Tech Corp., *How Optical Components Work*, www.chelix.com/products, 2002-2003 (1 pg.).

Chelix Tech Corp., *Technical Background*, www.chelix.com/products, 2002-2003 (1 pg.).

Chelix Tech Corp., *How CLCs Work*, www.chelix.com/products, 2002-2003 (2 pgs.).

Chelix Tech Corp., *Reflection & Polarization*, www.chelix.com/products, 2002-2003 (2 pgs.).

Chelix Tech Corp., *Switchable CLCs*, www.chelix.com/products, 2002-2003 (1 pg.).

Chelix Tech Corp., *A Short History of CLCs*, www.chelix.com/products, 2002-2003 (2 pgs.).

Chelix Tech Corp., *Polarization*, www.chelix.com/products, 2002-2003 (2 pgs.).

* cited by examiner

SENSING LIGHT

BACKGROUND

Many applications may utilize one or more objects such as tokens. Distinguishing between objects or distinguishing authentic objects from counterfeit objects may be costly and difficult.

DETAILED DESCRIPTION OF EXAMPLE EMBODIMENTS

Figure 1:
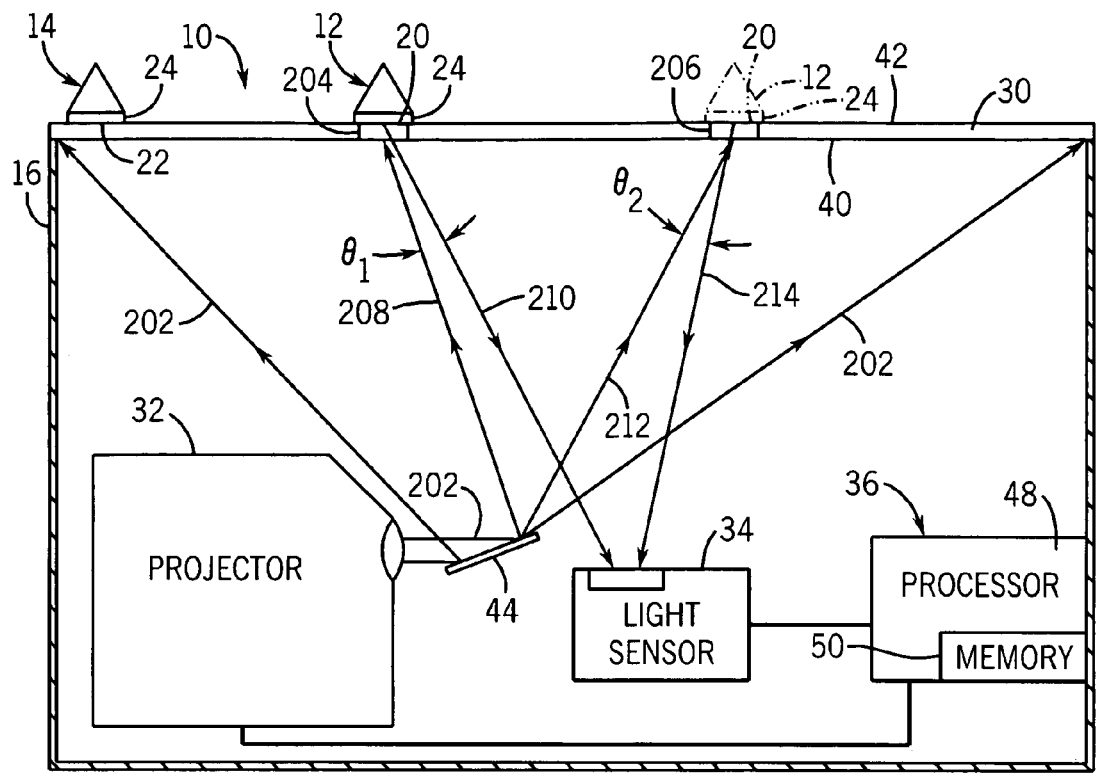
FIG. 1 is a sectional view schematically illustrating an embodiment of an object identification system according to one exemplary embodiment.

FIG. 1 schematically illustrates an embodiment of an object identification system 10 which is configured to identify and potentially distinguish between various objects such as tokens. System 10 generally includes objects 12, 14 and identifier 16. Objects 12, 14 comprise individual members movable relative to one another and with respect to identifier 16. Objects 12 and 14 include surfaces 20 and 22, respectively. Surfaces 20 and 22 are configured such that light reflected off of surfaces 20 and 22 at different angles with respect to incident light exhibits different characteristics. In one embodiment, light reflected off of surfaces 20 and 22 at different angles with respect to incident light will exhibit different color. For example, light reflected off of surface 20 at a first angle with respect to its incident light will exhibit a first color and the same light reflected off of surface 20 at a second distinct angle with respect to its incident light will exhibit a second distinct color. The same applies for surface 22. In one embodiment, surfaces 20 and 22 are configured such that the same light reflected off of surfaces 20 and 22 at the same angle with respect to incident light will exhibit the same characteristics such as the same color. In another embodiment, surfaces 20 and 22 are configured such that the same light reflected off of surfaces 20 and 22 at the same angle with respect to incident light will exhibit different characteristics such as different colors.

In the embodiment illustrated, surfaces 20 and 22 each include a color shifting ink 24. Color shifting ink 24, also known as "color flop" ink, causes light reflected off of surfaces 20 and 22 at different angles with respect to incident light to exhibit different color. In one embodiment, color shifting ink 24 is supplied by Chelix Technologies Corporation of Sunnyvale, Calif., a subsidiary of Reveo, Inc. In other embodiments, other color shifting inks may be used or other materials or surface configurations may be employed that are configured such that light reflected off surfaces 20 and 22 at different angles with respect to incident light exhibit different characteristics.

In the particular embodiment illustrated, objects 12 and 14, which comprise individual structures, are configured to rest upon identifier 16. In one embodiment, surfaces 20 and 22 of objects 12 and 14, respectively, are configured to rest or lay upon identifier 16. Objects 12 and 14 are further configured to be moved and located at various locations upon identifier 16. In one embodiment, objects 12 and 14 comprise 3-dimensional objects or structures which extend or project away from surfaces 20 and 22 by a distance of at least 0.25 inches, facilitating grasping of such objects by a person's fingers for movement along identifier 16. In one embodiment, such objects 12 and 14 may comprise tokens as part of an electronic game or application. Example of game piece tokens include chess pieces and checker pieces. In other embodiments, objects 12, 14 may comprise substantially 2-dimensional members such as cards and the like.

According to one embodiment, objects 12 and 14 are identical to one another. In such an embodiment, the light changing characteristics of surfaces 20 and 22 may be used to identify objects 12 and 14 as being of a common family or as being authorized or authentic. In another embodiment, objects 12 and 14 may be different from one another except for identical surfaces 20 and 22 which may still be used to identify objects 12 and 14 as being of a common family or as being authorized or authenticated. In yet another embodiment, objects 12 and 14 have the same or different configurations and surfaces 20 and 22 with different light changing characteristics that may be used to identify and specifically address objects 12 and 14 during communication with objects 12 and 14.

Identifier 16 generally comprises a device configured to cause light to be reflected off of surface 20 or surface 22 of objects 12, 14 at different angles with respect to its incident light and to identify object 12 and/or object 14 based upon different characteristics of the sensed reflected light. In the example shown in FIG. 1, identifier 16 generally includes screen 30, projector 32, light sensor 34 and controller 36. Screen 30 comprises a component configured to receive light projected from projector 32 and to provide a surface upon which images may be formed. Screen 30 is further configured to facilitate interaction with objects 12, 14. In the particular example shown, screen 30 comprises one or more layers of materials configured to scatter light from projector 32 such that light received from projector 32 on a first side of screen 30 may be viewed on a second, opposite side of screen 30. In one embodiment, screen 30 comprises frosted glass. In one embodiment, screen 30 comprises a screen commercially available from Da-Lite Screen Company of Warsaw, Ind., under the trade name Da-100.

Screen 30 includes a first surface 40 facing projector 32 and light sensor 34 and a second opposite surface 42 facing outward. Surface 42 is configured to facilitate interaction with objects 12, 14. Screen 30 is further configured to enable light emitted from projector 32 to pass through and be reflected off of surface 20 of object 12 or surface 22 of object 14. In the particular example shown, surface 42 is supported and arranged in a substantially horizontal orientation, enabling objects, such as objects 12 and 14, to rest upon surface 42. Although surface 42 and screen 30 are illustrated as being substantially horizontal, surface 42 may alternatively be supported at other orientations. For example, surface 42 may alternatively be inclined, declined or vertical. In other embodiments, surface 42 may be convex or concave. Although surfaces 40 and 42 are illustrated as being substantially parallel to one another, surfaces 40 and 42 may alternatively have other shapes or configurations. Although screen 30 is illustrated as being positioned between objects 12, 14 and projector 32, in other embodiments, screen 30 may alternatively be arranged such that projector 32 projects light onto surface 42 with objects 12, 14 supported between surface 42 and projector 32. In such an alternative embodiment, identifier 16 would include an additional light source for directing light at surface 20 or surface 22 of objects 12, 14. Such an additional light source may produce light or electromagnetic radiation within or outside the visible spectrum.

Projector 32 comprises a device configured to project light towards screen 30 so as to form an image upon screen 30. In the particular example shown, projector 32 is also configured to serve as a source of light that is reflected off of objects, such as objects 12, 14, resting upon screen 30, wherein the reflected light is sensed by light sensor 34. In the embodiment shown in FIG. 1, projector 32 projects light which is first reflected off of mirror 44 to redirect the light towards screen 30. In other embodiments, projector 32 may alternatively be configured to direct light towards screen 30, enabling mirror 44 to be omitted. In still other embodiments, other optic devices may be used to transmit light from projector 32 onto screen 30. In the embodiment shown, projector 32 comprises a digital light processing (DLP) projector. In other embodiments, projector 32 may comprise other forms of projectors.

Light sensor 34 generally comprises a device configured to receive light and to sense the characteristics of light. In the particular example shown, light sensor 34 is configured to sense the characteristics of light reflected from objects upon screen 30. Based upon the sensed light, light sensor 34 generates electrical signals which are communicated to controller 36. In one embodiment, light sensor 34 comprises a digital camera. In other embodiments, light sensor 34 may comprise other light sensitive devices.

Controller 36 generally comprises a device in communication with light sensor 34 configured to compare signals received from light sensor 34. In the example shown, controller 36 is initially configured to generate control signals which direct operation of projector 32 and light sensor 34. Controller 36 includes processor 48 and memory 50. Processor 48 comprises a processor unit. For purposes of this disclosure, the term "processor unit" shall mean a presently available or future developed processing unit that executes sequences of instructions contained in a computable readable medium such as memory 50. Execution of the sequences of instructions causes the processing unit to perform steps such as generating control signals. In the particular example shown, processor 48 is specifically configured to compare signals received from light sensor 34 to determine an actual or sensed relationship of one or more characteristics of light reflected from surface 20 of object 12 or surface 22 of object 14 at different angles. Processor 48 is further configured to compare the sensed relationship with data stored in memory 50 to identify one or both of objects 12, 14.

Memory 50 comprises a computer readable medium associated with processor 48 and configured to provide instructions for processor 48. In the particular example shown, memory 50 is further configured to store data relating to identification of objects placed upon screen 30. In the example shown, memory 50 is configured to store identification information for objects of system 10. For example, in one embodiment, memory 50 is configured to store identification relationship values for objects that are authorized to be used as part of system 10. For example, memory 50 may store data indicating that for an object to be authentic, light reflected from the object at a first angle is to be a first color and that light reflected from the same object at a different angle is to exhibit a second color. In such a scenario, processor 48 would compare the actual color characteristics of a particular object as sensed by light sensor 34 to the data stored in memory 50 to determine whether the particular object was authentic or otherwise authorized for use as part of system 10.

In one embodiment, memory 50 may comprise random access memory (RAM). In another embodiment, memory 50 may comprise a mass storage device or some other persistent storage. In still other embodiments, hardwired circuitry may be used in place of or in combination with software instructions to direct the operation of processor 48. Processor 48 is not limited to any specific combination of hardware circuitry and software, nor to any particular source for the instructions executed by processing unit 48.

Figure 2:
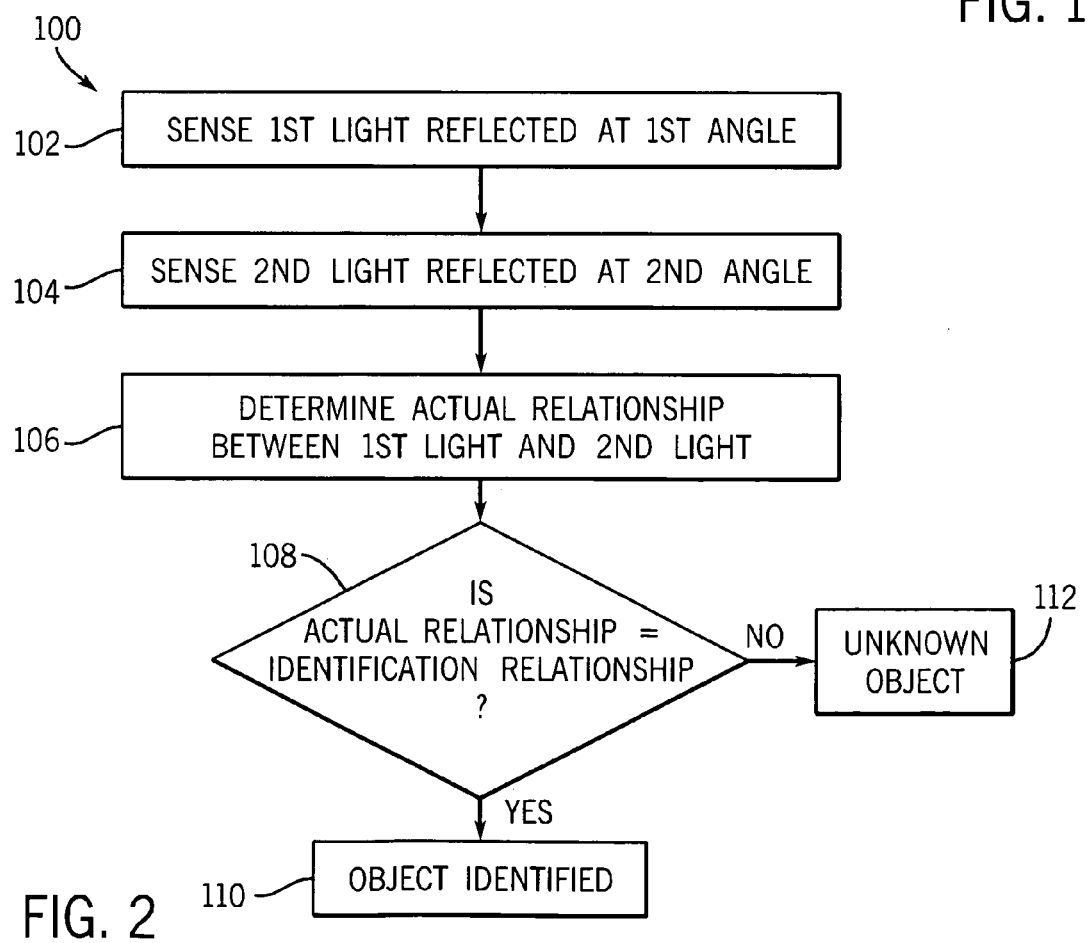
FIG. 2 is a flowchart illustrating an embodiment of a process for identifying objects according to one exemplary embodiment.

FIG. 2 is a flowchart illustrating an embodiment of a process 100 using light sensor 34 and controller 36. As indicated by step 102, sensor 34 senses the first light reflected off of surface 20 of object 12 at a first angle. As a result, sensor 34 generates signals which are communicated to processor 48 which stores such signals in memory 50. As indicated by step 104, sensor 34 senses a second light reflected from surface 20 of object 12 at a second angle. Based upon the sensed second light, sensor 34 generates signals which are communicated to processor 48. At this point, processor 48 may or may not store the second signals in memory 50.

As indicated by step 106, processor 48 determines an actual relationship data between the first light and the second light based upon the first signals and second signals. For example, signals received from sensor 34 may indicate the color wavelength values of the first light and the second light, wherein processor 48 would determine the relationship between the first wavelength value and the second wavelength value.

As indicated by step 108, processor 48 obtains stored identification relationship data. For example, identification relationship data may indicate that light reflected from an authorized object at the first angle and the light reflected from the object at the second angle should have a change in wavelength of a certain amount. As indicated by step 108, processor 48 compares the actual relationship as determined from the first signal and the second signal received from light sensor 34 to the stored identification relationship.

In the particular example shown, the identification relationship data is stored in memory 50 which is accessed by processor 48. In another embodiment, identification relationship data may be stored in other memories. For example, identification relationship data may alternatively be stored in a universal serial bus (USB) plug-in memory such as a USB flash drive, a dongle mechanism which generally comprises a hardware key that plugs into a parallel or a serial part, a special key diskette or some form of read-only memory. As will be described hereafter with respect to FIG. 5, identification relationship data may also be stored in a memory associated with the object itself, wherein the object and processor 48 are configured to communicate with one another.

As indicated by step 110, if the actual relationship is equal to the identification relationship, a particular object from which light was reflected is identified as an object authorized or authenticated for use as part of system 10. In one embodiment, the identification relationship may be a range of values or the object may be identified as being authentic or authorized if the actual relationship is within a predetermined percentage of the stored identification relationship. As indicated by step 112, if the actual relationship as determined from light reflected from an object at different angles is not equal to the stored identification relationship (or within the range of the identification relationship or within a predetermined percentage of the identification relationship), the object is unknown or not recognized as being authorized for use in system 10.

As indicated by steps 102 and 104 shown in FIG. 2, sensor 34 senses light reflected from an object at different angles. FIG. 1 further illustrates one example configuration for enabling sensor 34 to sense light reflected from an object at different angles. As shown by FIG. 1, controller 36 generates control signals which are communicated to projector 32. In response to receiving such control signals, projector 32 projects light 202 which is reflected off of mirror 44 and which forms an image upon screen 30. The image upon screen 30 includes indicators 204 and 206. Indicators 204 and 206 indicate the positions upon surface 42 at which object 12 should sequentially be located during identification of object 12. Indicators 204 and 206 may be simultaneously projected or may be projected upon screen 30 at different times. Indicators 204, 206 may be identical to one another or may be different. In one embodiment, indicators 204 and 206 may be different. In one embodiment, indicators 204 and 206 may include arrows. In another embodiment, indicators 204 and 206 may include circles, squares or other shapes otherwise indicating the positioning locations for object 12.

When object 12 is placed upon the location indicated by indicator 204 as shown in FIG. 1, light 208 from projector 32 is reflected off of surface 20. A portion 210 of the light 202 is received by sensor 34 and is at a first angle $\Theta_1$ with respect to its incident light 208. Sensor 34 generates signals based upon characteristics of light 210 having angle $\Theta_1$ and communicates such signals to controller 36.

As shown in phantom in FIG. 1, object 12 is subsequently repositioned by a user to a different position upon screen 30 based upon the location indicated by indicator 206. As a result, light 202 is reflected off of surface 20. A portion 212 of the light reflected off of surface 20 is received and sensed by light sensor 34. Portion 214 of the reflected light has a second distinct angle $\Theta_2$ with respect to its incident light. In response to receiving light 214, light sensor 34 communicates signals based upon the characteristics of light 214 and communicates such signals to processor 48. Thereafter, processor 48 performs the steps indicated in steps 106-112 shown and described with respect to FIG. 2.

Figure 3:
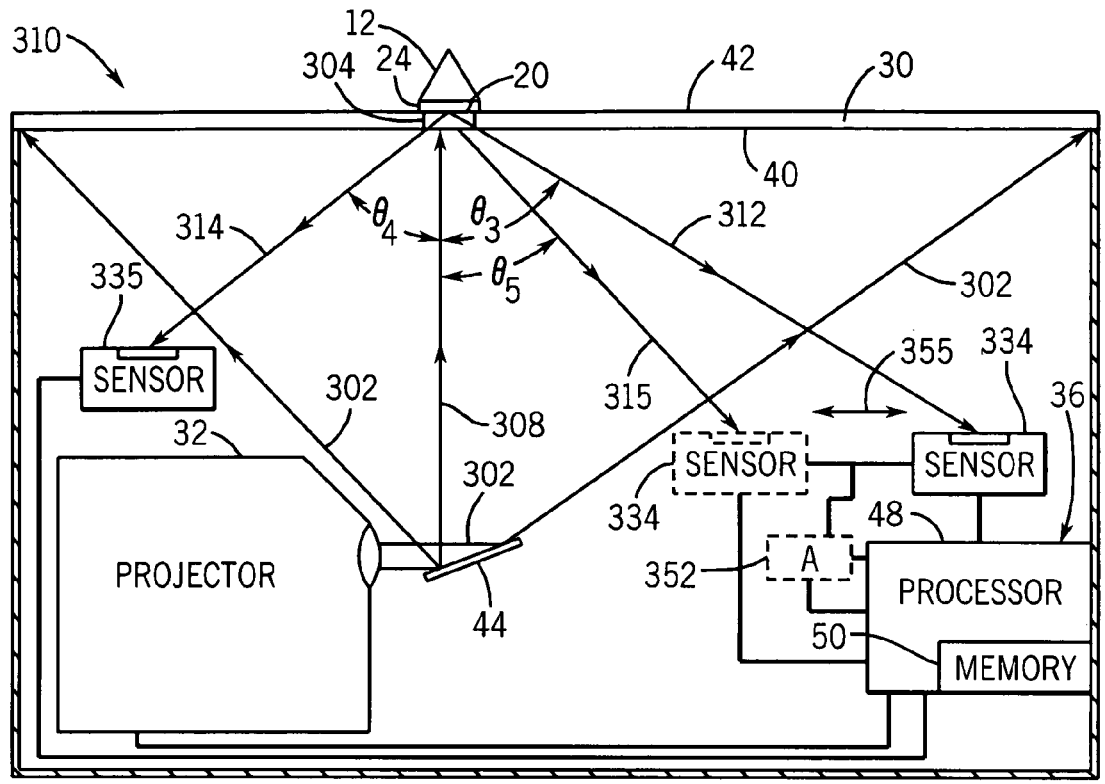
FIG. 3 is a sectional view schematically illustrating another embodiment of the object identification system of FIG. 1 according to one exemplary embodiment.

FIG. 3 schematically illustrates system 310, another embodiment of system 10 shown in FIG. 1. System 310 is similar to system 10 except that system 310 is additionally configured to facilitate the identification of object 12 (or object 14) by sensing light reflected off of object 12 at different angles without a person moving object 12. As shown by FIG. 3, system 310 is similar to system 10 except that system 310 includes light sensors 334 and 335 in lieu of light sensor 34. Those remaining components of system 310 which correspond to similar components of system 10 are numbered similarly.

Light sensors 334 and 335 facilitate sensing of light reflected from object 12 at different angles without movement of object 12. According to one example scenario of operation of system 310, controller 36 generates control signals directing projector 32 to project light 302 which is reflected off mirror 44 and forms an image upon screen 30. The image upon screen 30 includes an indicator 304 which indicates a predetermined or pre-established position for object 12 upon screen 30 to identify object 12. Portion 308 of light 302 is reflected off of surface 20 of object 12. A portion 312 of reflected light from surface 20 is received and sensed by light sensor 334. Light 312 has an angle $\Theta_3$ with respect to its incident light 308. Upon receiving light 312, sensor 334 generates and communicates signals to controller 36 based upon the sensed characteristics of light 312, such as its color or wavelength.

As further shown by FIG. 3, portion 314 of the light reflected off of surface 20 is received by light sensor 335. Light 314 has an angle $\Theta_4$ with respect to its incident light 308 that is distinct from angle $\Theta_3$. In response to receiving light 314, sensor 335 generates and communicates signals to controller 36 based upon the characteristics of light 314, such as its color or wavelength. In one embodiment, light sensors 334 and 335 may simultaneously or near simultaneously receive light 312 and 314, respectively, and transmit signals to controller 36. In another embodiment, controller 36 may alternatively direct light sensors 334 and 335 to consecutively receive light 312 and 314, respectively, and to consecutively transmit signals to controller 36. Based upon such signals, controller 36 may carry out the steps 106-112 (shown in FIG. 2) in an attempt to identify object 12.

FIG. 3 schematically illustrates yet another embodiment of system 310. As indicated in phantom, in lieu of light sensor 335, system 310 may alternatively include actuator 352. Actuator 352 comprises a mechanism configured to move light sensor 334 between a first position (shown with solid lines) and a second position (shown in phantom lines). In one embodiment, actuator 352 comprises a mechanism configured to linearly move light sensor 334 between the first position and the second position as indicated by arrows 355. In yet another embodiment, actuator 352 may alternatively comprise a mechanism configured to rotate or pivot light sensor 334 between the first position and the second position. In one embodiment, actuator 352 may comprise a solenoid. In still another embodiment, actuator 352 may comprise a hydraulic or pneumatically operated piston cylinder assembly. In still another embodiment, actuator 352 may include an electric motor and a transmission (not shown) including one or more cams configured so as to move light sensor 334 between the first and second positions. In another embodiment, actuator 352 may include a piezo mechanism.

As discussed above, when light sensor 334 is in the first position, portion 312 of light reflected from surface 20 is received by light sensor 334 and has an angle $\Theta_3$ with respect to its incident light 308. Light sensor 334 generates signals based upon light 312 and transmits such signals to controller 36. When light sensor 334 is in the second position (shown in phantom), light sensor 334 receives a portion 315 of light reflected from surface 20. Light 315 has an angle $\Theta_5$ with respect to its incident light 308. Light sensor 334 generates signals based upon one or more characteristics, such as color or wavelength, of light 315 and communicates such signals to controller 36. Thereafter, controller 36 may carry out the steps 106-112 shown in FIG. 2 in an attempt to identify object 12.

Figure 4:
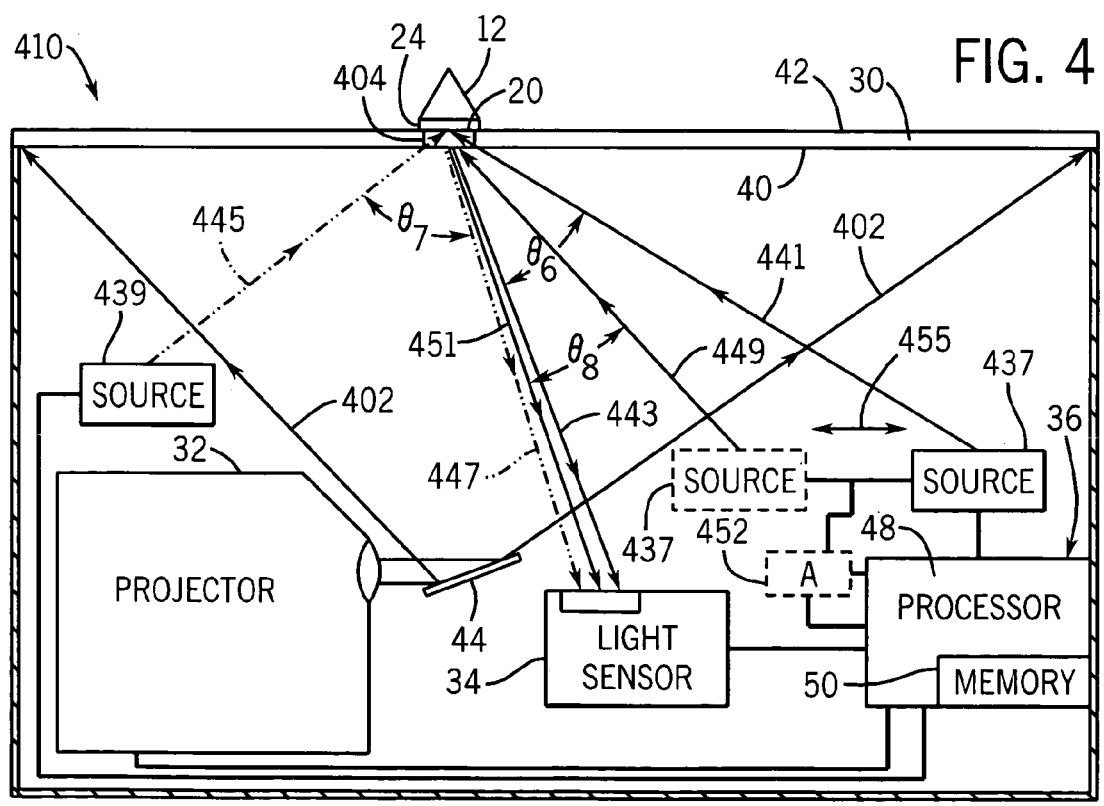
FIG. 4 is a sectional view schematically illustrating yet another embodiment of the object identification system of FIG. 1 according to one exemplary embodiment.

FIG. 4 schematically illustrates system 410, another embodiment of system 10 shown in FIG. 1. Like system 310 shown in FIG. 3, system 410 is configured to facilitate identification of object 12 without object 12 being repositioned upon screen 30. System 410 is similar to system 10 except that system 410 additionally includes light sources 437 and 439. Those remaining components of system 410 which correspond to similar components of system 10 are numbered similarly. Light sources 437, 439 comprise devices configured to emit or project light towards surface 20 of object 12 from different locations such that reflected light received by light sensor 34 is at different angles. In one embodiment, light sources 437 and 439 are configured to project light directly at surface 20. In another embodiment, sources 437, 439 additionally include one or more mirrors or optic systems focusing or redirecting light at surface 20.

As shown by FIG. 4, controller 36 generates control signals directing projector 32 to project light 402 which is redirected by mirror 44 so as to form an image upon screen 30. The image upon screen 30 includes indicator 404 which indicates a predetermined position at which object 12 should be located during its identification. Controller 36 further generates control signals directing light source 437 to project light 441 towards surface 20 of object 12. A portion 443 of the light 441 reflected from surface 20 is received and sensed by light sensor 34. Light 443 has an angle $\Theta_6$ with respect to its incident light 441. Upon receiving light 443, light sensor 34 generates signals based one or more characteristics of light 443, such as its color or wavelength, and transmits such signals to controller 36.

As shown in phantom in FIG. 4, controller 36 subsequently generates control signals directing light from light source 437 to either be blocked or terminated and directing light source 439 to project light 445 towards surface 20 of object 12. A portion 447 of light 445 is reflected off of surface 20 of object 12 is received and sensed by light sensor 34. Reflected light 447 has an angle $\Theta_7$ with respect to incident light 445. Upon receiving light 447, light sensor 34 generates signals based upon one or more characteristics of light 447, such as its color or wavelength, and transmits such signals to controller 36. Controller 36 may then carry out steps 106-112 shown in FIG. 2 in an attempt to identify the object shown and described with respect to FIG. 2 in an attempt to identify object 12.

FIG. 4 further illustrates another embodiment of system 410 with phantom lines. As shown in phantom by FIG. 4, system 410 may alternatively include actuator 452 while omitting light source 439. Actuator 452 comprises a mechanism configured to move light source 437 between a first position (shown in solid lines) and a second position (shown in phantom lines). In one embodiment, actuator 452 comprises a linear actuator configured to move light source 437 between the first position and the second position as indicated by arrows 455. In another embodiment, actuator 452 may comprise a rotary actuator configured to rotate light source 437 between the first position and the second position. In one embodiment, actuator 452 may comprise a solenoid or a hydraulic or pneumatic cylinder-piston assembly. In still another embodiment, actuator 452 may comprise an electric motor including a transmission having one or more cams (not shown) configured to move light source 437 between the first and second positions. In one embodiment, actuator 452 may comprise a piezo mechanism.

As noted above, when light source 437 is in the first position (shown in solid lines), reflected light 443 has an angle $\Theta_6$ with respect to incident light 441. Upon being received by light sensor 34, light sensor 34 transmits signals based upon one or more characteristics of light 443 to controller 36.

As shown in phantom lines in FIG. 4, controller 36 generates control signals directing actuator 452 to move light source 437 to the second position. In the second position, light source 437 projects light 449 towards surface 20 of object 12. A portion 451 of incident light 449 reflected from surface 20 is received by light sensor 34. Reflected light 451 has an angle $\Theta_8$ with respect to incident light 449. Upon receiving and sensing reflected light 451, light sensor 34 generates signals based upon one or more characteristics, such as color or wavelength, of light 451 and transmits such signals to controller 36. Controller 36 may then carry out steps 106-112 as shown in FIG. 2 in an attempt to identify object 12.

Although system 410 is illustrated as utilizing two light sources 437, 439 in addition to projector 32, in other embodiments, projector 32 may alternatively serve as a light source, enabling light source 439 to be omitted. Although indicators 204, 206, 304 and 404 are illustrated and described as being formed as part of an image made by projector 32, one or more of indicators 204, 206, 304 and 404 may alternatively be provided by other methods. For example, one or more of indicators 204, 206, 304 and 404 may alternatively be permanently indicated upon screen 30. For example, one or more permanent location identifiers may be formed upon screen 30 with differently colored coatings such as paint, ink and the like, by differently colored materials such as different polymers and the like or by visible surface texture variations such as roughened arrow, ring, rectangle and the like. In still other embodiments, use of indicators 204, 206, 304 and 404 may be omitted where controller 36 is configured to otherwise determine a position of object 12 upon screen 30 using light sensor 34, 334 or 335 and where processor 36 is also configured to determine the angle between an incident light and a reflected portion of the light received by light sensor 34. In particular embodiments, projector 32 may be omitted or may be positioned at other locations such as on an opposite side of screen 30 as compared to light sensor 34. In some embodiments, projector 32 may be omitted where other devices or methods are utilized to form image upon screen 30.

Figure 5:
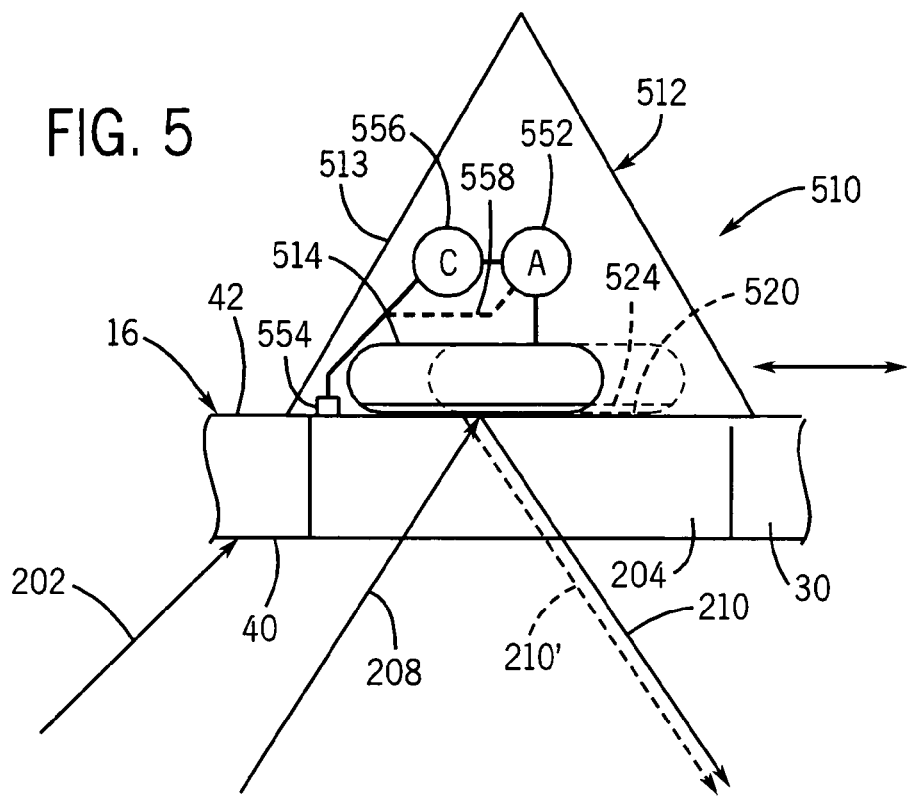
FIG. 5 is a fragmentary sectional view schematically illustrating another embodiment of an object of the system of FIG. 1 according to one exemplary embodiment.

FIG. 5 schematically illustrates portions of object identification system 510, another embodiment of system 10 shown in FIG. 1. System 510 is similar to system 10 except that system 510 includes object 512 in lieu of object 12. Those remaining components of system 510 which are illustrated and which correspond to components of system 10 are numbered similarly. As shown by FIG. 5, object 512 comprises an individual member movable relative to other objects with respect to identifier 16. Object 512 is configured to be placed and to rest upon surface 42 of screen 30 such that light may be reflected off of object 512. Object 512 generally includes body 513, movable member 514 having surface 520, actuator 552, trigger 554 and controller 556. Body 513 comprises a structure which supports and houses the remaining components of object 512 such as member 514, actuator 552, trigger 554 and controller 556. In one embodiment, body 513 comprises a generally 3-dimensional structure. In one embodiment, body 513 is configured as a token, enabling object 512 to be grasped, lifted and moved. In one embodiment, body 513 has a height of at least 0.25 inches.

Movable member 514 comprises a member or structure movably supported by body 513 such that light may be reflected off of its surface 520. In the particular example shown, member 514 is movable between a first position shown in solid and a second position shown in phantom. Surface 520 of body 514 is configured such that light reflected off of surface 520 at the same angle with respect to incident light will exhibit the same characteristics such as the same color. Surface 520 is also configured such that the same light reflected off of surface 520 at different angles with respect to incident light will exhibit different characteristics such as different colors. In one particular embodiment, surface 520 includes a color shifting ink 524.

Actuator 552 comprises a mechanism supported by body 513 and configured to move member 514 between the first position and the second position. In one embodiment, actuator 552 may comprise a piezo device operably coupled to member 514. In another embodiment, actuator 552 may comprise other actuation mechanisms such as those utilizing motors, cylinder-piston assemblies, solenoids and the like.

Trigger 554 comprises a mechanism configured to respond to placement of object 512 upon screen 30 such that actuator 552 moves member 514 between the first position and the second position. In one embodiment, trigger 554 may comprise an optical sensor configured to transmit signals to controller 556 in response to object 512 being placed upon screen 30. In another embodiment, trigger 554 may comprise a pressure sensor which is compressed or moved against a biasing spring in response to object 512 being placed upon screen 30, wherein depressing the projecting sensor causes signals to be communicated to controller 556. In other embodiments, other forms of sensing devices or trigger mechanisms may be employed to detect placement of object 512 upon screen 30.

Controller 556 comprises a processing unit configured to generate control signals directing the operation of actuator 552. In one embodiment, controller 556 generates control signals based upon signals it receives from trigger 554 so as to cause actuator 552 to actuate member 514 between the first position and the second position. As indicated by broken line 558, controller 556 may be omitted where trigger 554 is directly connected to actuator 552 such that depressing or other actuation of trigger 554 automatically causes actuator 552 to move member 514. For example, in one embodiment, trigger 554 may comprise a switch which is actuated upon object 512 being placed upon screen 30 such that actuation of the switch automatically causes actuator 552 to move member 514. In still other embodiments, trigger 554 may be omitted, wherein controller 556 generates control signals causing actuator 552 to periodically move member 514 between the first and second positions. For example, controller 556 may include an internal timer causing controller 556 to generate control signals such as actuator 552 which moves member 514 on a timed basis. In still other embodiments, trigger 554 and controller 556 may be omitted where actuator 552 is configured to continuously or periodically move member 514 between the first and second positions without further input from a controller or a trigger mechanism.

In operation, projector 32 (shown in FIG. 1) projects light 202 off of mirror 44 and onto screen 30 to form an image upon screen 30 which includes indicator 204. As noted above, in other embodiments, indicator 204 may be provided in other ways or may be omitted. Object 512 is placed upon screen 30. In response to object 512 being placed upon screen 30, trigger 554 is tripped, causing a signal to be transmitted to controller 556. Controller 556 generates control signals causing actuator 552 to move from a first position shown in solid lines to a second position shown in phantom lines. Prior to movement of member 514 by actuator 552, a light source, such as projector 32 projects an incident light 208 upon surface 520 which is altered by color shifting ink 524 and is reflected as reflected light 210. As discussed above with respect to FIG. 1, reflected light 210 is received by light sensor 34 (shown in FIG. 1) and signals transmitted to controller 36 are analyzed, modified and/or stored in memory 50 by processor 48 (shown in FIG. 1).

After movement of member 514 by actuator 552, a light source, such as projector 32 (shown in FIG. 1) continues to project an incident light 208 upon surface 524 of the moved member 514 which is altered and reflected as reflected light 210'. Although illustrated as two separate lines, lights 210 and 210' have the same angle with respect to incident light 208. Although line 210 and 210' have the same angle with respect to incident light 208, light 210 has differing characteristics, such as a different color, as a result of being reflected off of a different portion of surface 520 having one or more different surface treatments such as different color shifting inks. The difference or relationship between reflected light 210 and 210' as detected by light sensor 34 and compared by processor 48 (shown in FIG. 1) may be compared to a stored identification relationship value contained in memory 50 or other memory. If the actual relationship between light 210 and 210' and a previously determined or known stored identification relationship value are the same or within a predefined range of one another, processor 48 may identify object 512 as an authentic or otherwise authorized object for use as part of system 510. Alternatively, if the actual relationship between light 210 and 210' is not equal to or out of a predefined range or percentage of the stored identification value, object 512 remains as an unknown object not generally authorized for use with system 510.

Although the above operation describes member 514 as being moved by actuator 552 in response to control signals from controller 556 based upon signals from trigger 554, member 514 may alternatively be moved by actuator 552 in direct response to actuation of trigger 554 (without controller 556) or may be moved by actuator 552 on a periodic, timed or continuous basis.

Figure 6A:
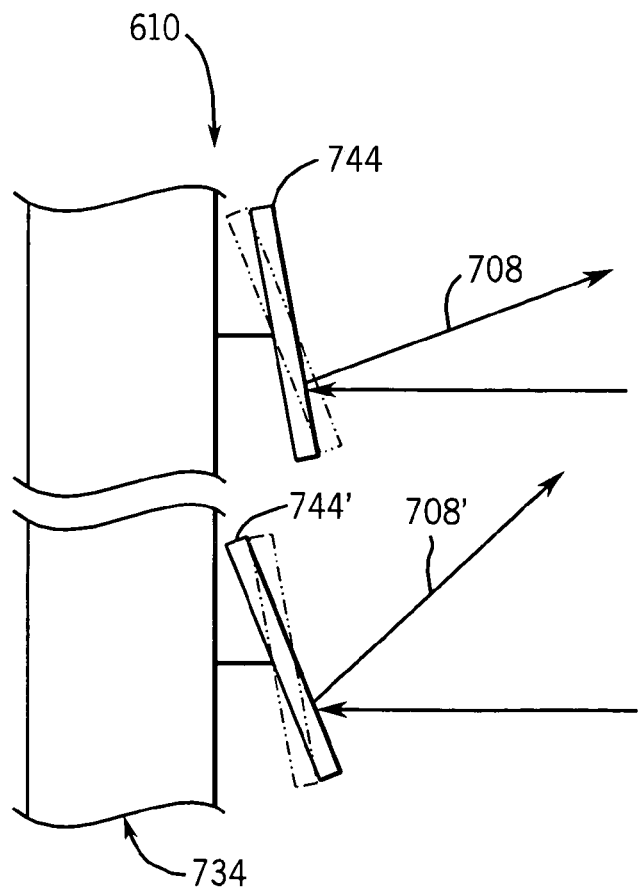
FIG. 6A is a fragmentary sectional view of one embodiment of a projector of the system of FIG. 6 according to one exemplary embodiment.
Figure 6B:
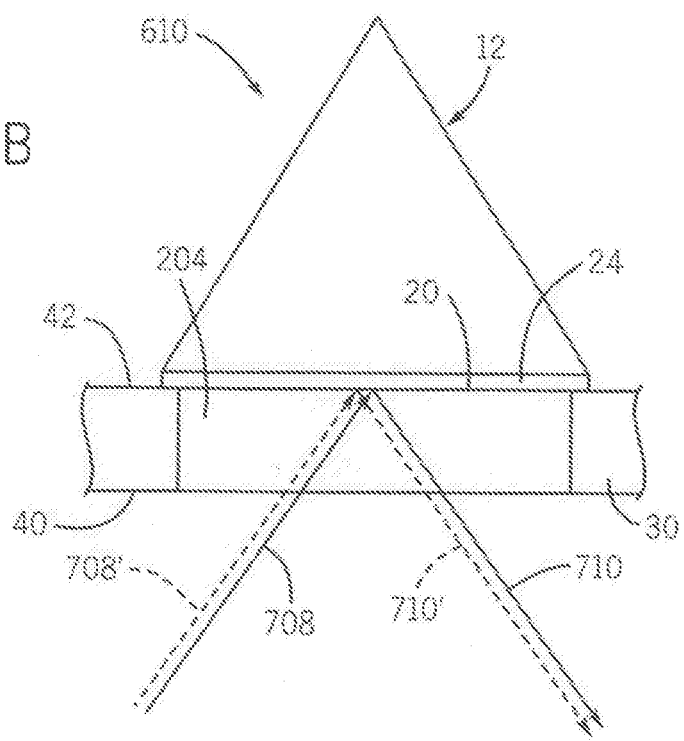
FIG. 6B is a fragmentary sectional view of an embodiment of an object upon a screen of the system of FIG. 6 according to one exemplary embodiment.
Figure 6:
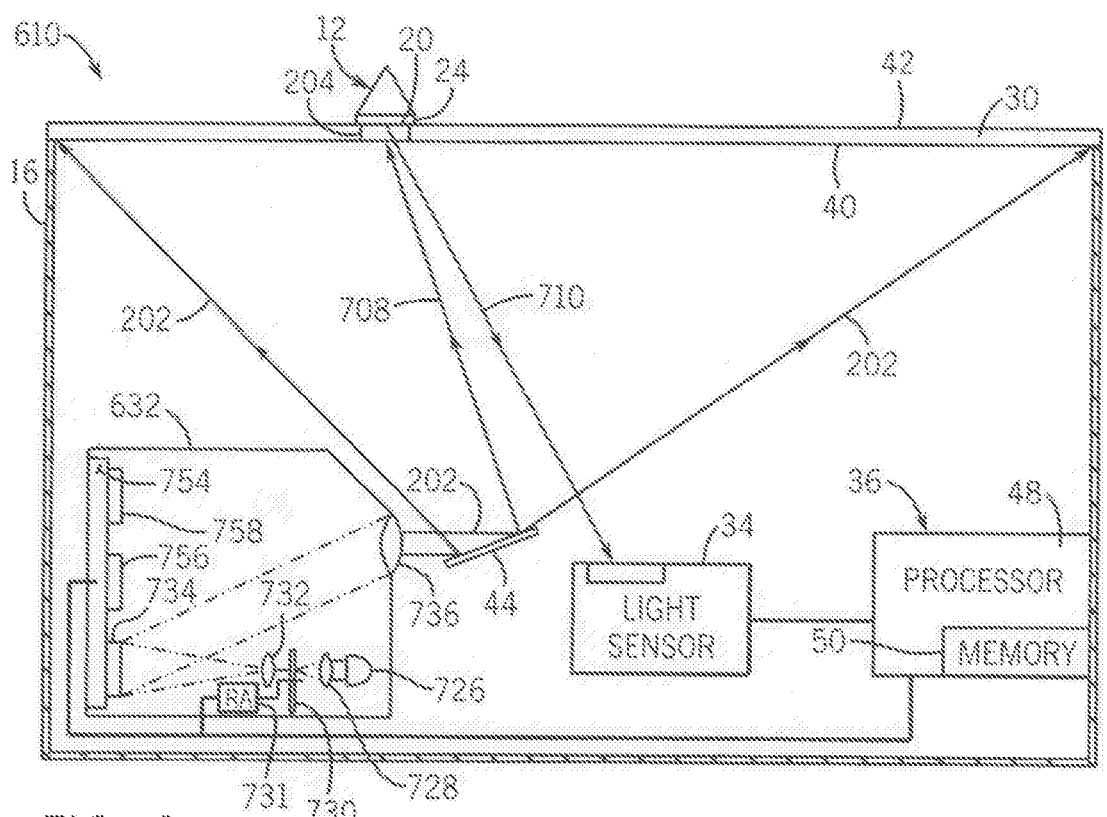
FIG. 6 is a sectional view schematically illustrating another embodiment of the object identification system of FIG. 1 according to one exemplary embodiment.

FIGS. 6, 6A and 6B schematically illustrate object identification system 610, another embodiment of system 10. System 610 is similar to system 10 except that system 610 includes a projector 632 or other light source configured to direct different incident light, such as incident light having different colors, upon surface 20 of object 12, wherein surface 20 alters the characteristics of the incident light in different ways as the light is being reflected and detected by light sensor 34. For example, in one embodiment, projector 632 may direct a first incident light having a first color onto surface 20. Surface 20 alters the first incident light such that the reflected light has a second color and is detected by light sensor 34. Projector 632 may subsequently direct a second incident light having a third color upon surface 20. Surface 20 alters the second incident light such that the reflected light has a fourth color that is detected by light sensor 34. In response to receiving the altered and reflected first incident light having the second color, light sensor 34 transmits signals to processor 48 which stores data corresponding to the characteristics of the first altered and reflected incident light in memory 50 or other memory. In response to receiving the second altered and reflected incident light having the fourth color, light sensor 34 transmits signals to processor 48. Processor 48 determines an actual relationship between the first altered and reflected incident light and the second altered and reflected incident light. This determined relationship is compared to a stored identification relationship value to identify object 12 and to determine whether object 12 is authorized for use with system 610.

In such an example, processor 48 compares the relationship between the second color and the fourth color. In one embodiment, processor 48 further compares the relationship between the first color and the second color and the third color and the fourth color. Processor 48 compares the determined actual relationship to stored identification relationship values contained in memory 50 or other memory. If the determined actual relationship values are equal to or within a predetermined range of the stored identification relationship values, processor 48 identifies object 12 as an authentic object authorized for use with system 610. If the determined actual relationship values are not equal to or out of range with respect to a predetermined or stored identification relationship value, object 12 remains unknown and is treated as an unauthorized or unauthenticated object.

As shown by FIG. 6, in one particular embodiment, projector 632 may comprise a digital light processing (DLP) projector. In such an embodiment, projector 632 includes light source 726, optics 728, color wheel 730, rotary actuator 731, optics 732, digital micromirror device (DMD) 734 and projection lens 736. Light source 726 comprises a source of light such as an ultra high pressure (UHP) arc lamp and reflector configured to emit light toward optics 728. In other embodiments, other sources of light may be used such as metal halide lamps and the like. Optics 728 are generally positioned between light source 726 and color wheel 730. Optics 728 condenses the light from source 726 towards DMD 734. In one embodiment, optics 728 may comprise a light pipe positioned between light source 726 and color wheel 730.

Color wheel 730 comprises an optic component configured to sequentially image color. Color wheel 730 generally comprises a disk or other member having a plurality of distinct filter segments positioned about the rotational axis 740 of the wheel and arranged such that light from optics 728 passes through such filter segments towards DMD 734.

Rotary actuator 731 comprises a device configured to rotatably drive color wheel 730. In one embodiment, rotary actuator 731 includes a motor and an appropriate transmission for rotating color wheel 730 at a desired speed. In other embodiments, rotary actuator 731 may comprise other devices configured to rotatably drive color wheel 730.

Optics 732 comprises one or more lenses or mirrors configured to further focus and direct light that has passed through color wheel 730 towards DMD 734. In one embodiment, optics 732 may comprise lenses which focus and direct the light. In another embodiment, optics 732 may additionally include mirrors which re-direct light onto DMD 734.

In one embodiment, DMD 734 comprises a semiconductor chip covered with a multitude of minuscule reflectors or mirrors 744 (shown in FIG. 6A) which may be selectively tilted between "on" positions in which light is re-directed towards lens 736 and "off" positions in which light is not directed towards lens 36. The mirrors are switched "on" and "off" at a high frequency so as to emit a gray scale image. In particular, a mirror that is switched on more frequently reflects a light gray pixel of light while the mirror that is switched off more frequently reflects darker gray pixel of light. In this context "gray scale", "light gray pixel", and "darker gray pixel" refers to the intensity of the luminance component of the light and does not limit the hue and chrominance components of the light. The "on" and "off" states of each mirror are coordinated with colored light from color wheel 730 to project a desired hue of color light towards lens 736. The human eye blends rapidly alternating flashes to see the intended hue of the particular pixel in the image being created. In the particular examples shown, DMD 734 is provided as part of a DLP board 754 which further supports a processor 756 and associated memory 758. Processor 756 and memory 758 are configured to selectively actuate the mirrors of DMD 734. In other embodiments, processor 756 and memory 758 may alternatively be provided by or associated with controller 36.

Lens 736 receives selected light from DMD 734 and projects the reflected light towards mirror 44. Mirror 44 re-directs the light towards screen 30. In other embodiments, lens 736 may alternatively be configured to direct light towards screen 30, enabling mirror 44 to be omitted. Although projector 632 is illustrated and described as a DLP projector, projector 632 may alternatively comprise other projectors having other components configured such that projector 632 sequentially projects a series of colors towards screen 30 so as to form a visual image upon screen 30.

FIGS. 6A and 6B illustrate one example scenario of operation of object identification system 610. As shown by FIGS. 6 and 6A, mirrors 744 and 744' of DMD 734 are each actuated to a position or orientation such that projector 632 projects light 202 to form an image upon screen 30. As shown by FIG. 6A, a portion of mirrors 744 are at a first position such that projector 632 directs incident light 708 towards surface 20 of object 12. As shown in FIG. 6B, incident light 708 is altered by surface 20 such that its reflected light 710 has the distinct characteristic such as color. The altered and reflected incident light 710 is received by light sensor 34 (shown in FIG. 6).

Subsequently, processor 48 generates control signals causing mirror 744' to be moved or reoriented from the first position shown in phantom to a second position shown in solid. In the second position, mirror 744' cause projector 632 to project a second incident light 708' that is altered by surface 20 and is reflected as light 710'. The altered and reflected incident light 710' is received by light sensor 34 (shown in FIG. 6). As discussed above, processor 48 then compares the relationship between light 710 and 710' to a stored identification relationship value to identify object 12 and determine whether object 12 is authentic and authorized for use with system 610 or is unknown.

Overall, each of systems 10, 310, 410, 510 and 610 facilitate identification of one or more objects such as objects 12, 14 and 512. Systems 10, 310, 410, 510 and 610 identify objects by providing such objects with a surface that alters reflected light and by sensing relationships between the altered reflected light. In one embodiment, this is achieved by providing such surfaces with a color shifting ink.

Systems 10, 310 and 410 enable an angle between the incident light and the reflected light to be varied such that the change in the light at the different angles may be detected and used to identify the object. Systems 510 and 610 vary the altering of reflected light. System 510 moves the light altering surface of an object. System 610 selectively projects different incident light upon the surface of an object which is reflected and altered differently. Objects are identified by comparing relationships between the characteristics of the incident light and the altered reflected light. This identification may be used to distinguish between individual objects for addressing and communicating to such objects or for determining whether an object is authorized or authenticated for use. As a result, systems 10, 310, 410, 510 and 610 may be used to prevent counterfeit objects from being used with such systems.

Although the present disclosure has been described with reference to example embodiments, workers skilled in the art will recognize that changes may be made in form and detail without departing from the spirit and scope of the claimed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompass a plurality of such particular elements.

What is claimed is:

1. A method comprising:
    projecting an image onto a screen with a projector;
    resting an object on the screen, the object having an object surface configured to face the screen when the body is resting on the screen;
    sensing with a sensor a first light from the projector that is reflected off an object surface at a first angle with respect to first incident light and having a first wavelength;
    sensing with the sensor a second light from the projector that is reflected off the object surface at a second angle with respect to second incident light and having a second wavelength; and
    comparing the first light and the second light to identify the object.

2. The method of claim 1 further comprising authenticating the object based upon the comparison of the first light and the second light.

3. The method of claim 1 further comprising:
    sensing light reflected off the object surface while the object surface is at a first position; and
    sensing light reflected off the object surface while the object surface is at a second position.

4. The method of claim 1, wherein comparing the first light and the second light includes comparing the color of the first light with a color of the second light.

5. The method of claim 1, wherein the object surface includes color shifting ink.

6. An apparatus comprising:
    an object having a surface configured to reflect wavelengths of light which vary based upon an angle between first incident light and reflected light;
    at least one sensor configured to generate a first signal using a first light reflected from the surface of the object at a first angle with respect to first incident light and to generate a second signal using a second light reflected from the surface of the object at a second angle with respect to second incident light;
    a horizontal surface, wherein the object is configured to be rested upon the horizontal surface, selectively, at a first position and a second position; and
    a projector configured to generate an image on the horizontal surface including a first indicator and a second indicator, wherein the projector is on a first side of the surface and wherein the object is configured to rest against a second side of the horizontal surface, wherein the first indicator is configured to indicate the first position for the surface of the object at which the first signal is to be generated; and wherein the second indicator is configured to indicate the second position for the surface of the object at which the second signal is to be generated.

7. The apparatus of claim 6, wherein the surface includes color shifting ink.

8. The apparatus of claim 6, further comprising at least one light source configured to direct the first incident light and the second incident light at the surface of the object.

9. The apparatus of claim 6 further comprising:
    a memory;
    data stored in the memory; and
    a processing unit configured to identify the object based upon the data and at least one of the first signal and the second signal.

10. The apparatus of claim 9, wherein the processing unit is configured to compare the first signal to the second signal to determine a relationship and to compare the relationship with the data.

11. The apparatus of claim 6 further comprising at least one light source configured to direct the first incident light having a first color at the surface of the object and the second incident light having a second color at the surface of the object, wherein the at least one light sensor is configured to generate the first signal based upon the first light after it has reflected off the surface of the object and is configured to generate the second signal based upon the second light after it has reflected off the surface of the object.

12. The apparatus of claim 6 further comprising a projector configured to project the first incident light at the surface of the object and to subsequently project the second incident light at the surface of the object, the second incident light having at least one characteristic different than the first incident light, wherein the projector includes a digital micromirror device and wherein the digital micromirror device is in a first state and the projector projects the first incident light and a second state when the projector projects the second incident light.

13. An apparatus comprising:
    a screen;
    a first token configured to rest upon the screen, the token having a first body and a first surface configured to face the screen when the first token is resting upon the screen;
    a projector configured to project an image onto the screen;
    a memory;
    data stored in the memory; and
    a processing unit configured to identify the first token using the data and light from the projector reflected off the first surface at different angles with respect to associated incident light of the first token.

14. The apparatus of claim 13 further comprising at least one sensor configured to generate a first signal based upon light reflected at a first angle off the first surface and a second signal based upon light reflected at a second angle off the surface.

15. The apparatus of claim 13 further comprising a second token configured to rest upon the screen, the second token having a second body substantially similar to the first body and a second surface configured to face the screen when the second token is resting upon the screen.

16. The apparatus of claim 13, wherein the projector is configured to project the image such that the image includes a first indicator configured to visibly indicate to a person a first position for the first surface at which reflected light has a first angle and a second indicator configured to visibly indicate to the person a second position for the first surface at which reflected light has a second angle with respect to associated incident light for identification of the first token.

17. The apparatus of claim 13, wherein the screen includes a first indicator configured to visibly indicate to a person a first position for the first surface at which reflected light has a first angle and a second indicator configured to visibly indicate to the person a second position for the first surface at which reflected light has a second angle with respect to associated incident light for identification of the first token.

18. The apparatus of claim 13 wherein the first surface is configured such that same light reflected off the surface at different angles with respect to incident light exhibits different characteristics.

19. The apparatus of claim 18, wherein the first surface is movable and wherein the token further comprises an actuator configured to move the surface.

20. An object comprising:
a body configured to be manually rested upon a screen;
a surface configured to face the screen when the body is resting on the screen, the surface being configured such that same light reflected off a portion of the surface having uniform characteristics at different angles with respect to incident light, exhibits different characteristics; and
an actuator configured to move the surface.

21. The object of claim 20 further comprising a trigger configured to be actuated in response to the body being rested on the screen, wherein the actuator moves the surface in response to actuation of the trigger.

22. The object of claim 20, wherein the actuator is configured to continuously move the surface.

23. The object of claim 20, wherein the actuator is configured to periodically move the surface.

24. The object of claim 20, wherein the actuator is configured to move the surface relative to the body while the body is stationary with respect to the screen.

25. An apparatus comprising:
an object having a surface configured to reflect wavelengths of light which vary based upon an angle between first incident light and reflected light;
at least one sensor configured to generate a first signal using a first light reflected from the surface at a first angle with respect to incident light and to generate a second signal using a second light reflected from the surface at a second angle with respect to second incident light; and
a projector configured to project a first incident light at the surface and to subsequently project a second incident light at the incident surface, the second incident light having at least one characteristic different than the first incident light, wherein the projector includes a digital micromirror device and wherein the digital micromirror device is in a first state and the projector projects the first incident light and a second state when the projector projects the second incident light.

26. An object comprising:
a body configured to be manually rested upon a screen;
a surface configured to face the screen when the body is resting on the screen, the surface being configured such that same light reflected off the surface at different angles with respect to incident light exhibits different characteristics; and
an actuator configured to move the surface relative to the body while the body is stationary with respect to the screen.

* * * * *